United States Patent [19]
Hess et al.

[11] Patent Number: 6,127,534
[45] Date of Patent: *Oct. 3, 2000

[54] PRESSURE-MODULATED ION ACTIVITY

[75] Inventors: Robert A. Hess, Cambridge; James A. Laugharn, Jr., Winchester, both of Mass.

[73] Assignee: BBI BioSeq, Inc., West Bridgewater, Mass.

[*] Notice: This patent issued on a continued prosecution application filed under 37 CFR 1.53(d), and is subject to the twenty year patent term provisions of 35 U.S.C. 154(a)(2).

[21] Appl. No.: 09/010,892

[22] Filed: Jan. 22, 1998

Related U.S. Application Data

[63] Continuation-in-part of application No. 08/903,156, Jul. 30, 1997.

[51] Int. Cl.⁷ .......................... C07H 21/00; C07H 21/02; C07H 21/04
[52] U.S. Cl. .............................................................. 536/25.4
[58] Field of Search ............................................. 536/25.4

[56] References Cited

U.S. PATENT DOCUMENTS 5,003,047  3/1991  Yarmush et al. ....................... 530/413

FOREIGN PATENT DOCUMENTS

98/00032  1/1998  WIPO .

OTHER PUBLICATIONS

Eckert, C.A., "High Pressure Kinetics in Solution", Ann. Rev. Phys. Chem., vol. 23, pp. 239–264, 1972.
Howlett et al., "Pressure–induced Conformational–changes in an Antigen and an Antibody and the Implications on Their Use for Hyperbaric Immunoadsorption", Biochimica at Biophysica Acta, vol. 1159, No. 3, pp. 227–236, Oct. 1992.
Yarmush et al., "Immunoadsorption—Strategies for Antigen Elution and Production of Reusable Adsorbents", Biotechnology Progress, vol. 8, No. 3, pp. 168–178, May 1992.
Høiland, H., Pressure Dependence of the Volumes of Ionization of Carboxylic Acids at 25, 35 and 45° C. and 1–200 bar, J. Chem. Soc. Faraday Trans. I, vol. 70, No. 7, pp. 1180–1185, 1974.
Høiland, H., Volumes of Ionization of Dicarboxylic Acids in Aqueous Solution from Density Measurements at 25° C., J. Chem. Soc. Faraday Trans. I, vol. 71, No. 4, pp. 797–802, 1975.
Kauzmann et al., Volume Changes in Protein Reactions. II. Comparison of Ionization Reactions in Proteins and Small Molecules, J. Am. Chem. Soc., vol. 84, No. 10, pp. 1777–1788, May 1962.
Lewis et al., Influence of Pressure on the Equilibrium of Hydration of Aliphatiuc Aldehydes, J. Am. Chem. Soc., vol. 95, No. 20, pp. 6685–6688.
Olson et al., Bio/Technology, vol. 7(4), "Recovery of Antigens from Immunoadsorbents Using High Pressure", pp. 369–373, Apr. 1989.
Mozhaev et al., Trends Biotechol., vol. 12, "Exploiting the Effects of High Hydrostatic Pressure in Biotechnological Applications", pp. 493–501, Dec. 1994.
Gavalda et al., Enz. Microbial. Technol., vol. 18(1), "High–Pressure–Induced Modulation of the Antigenic Interactions Between Two beta–Galactosidases and Anti–beta–Galactosidase Antibodies", pp. 10–17, Jan. 1996.
Delben and Crescenzi, "The Ionization of Aliphatic Dicarboxylic Acids in Water," J. Solution Chem., 7(8): 1978.
Distèche, "Effects of Pressure on the Dissociation of Weak Acids," Symp Soc. Exp. Biol. 26:27–60, 1972.
Hamann and Lim, "The Volume Change of Ionization of Weak Electrolytes," Australian J. Chem., 7:329–334, 1954.
Hamann, "The Influence of Pressure on Ionization Equilibria in Aqueous Solutions," J. Solution Chem., 11(1):63–67, 1982.
Kauzmann et al., "Volume Changes in Protein Reactions . . . ," J. Am. Chem. Soc., 84:1777–1788, 1962.
Kitamura and Itoh, "Reaction Volume of Protonic Ionization for Buffering Agents . . . ," J. Solution Chem. 16(9):715–725, 1987.
Neuman et al., "Pressure Dependence of Weak Acid Ionization in Aqueous Buffers," J. Phys. Chem., 77(22):2687–2691, 1973.
Rasper and Kauzmann, "Volume Changes in Protein Reactions . . . ," J. Am. Chem. Soc., 84(10):1771–1777, 1962.
Srivastava et al., "Ionization Volumes by Means of Direct Dilatometry," J. Solution Chem., 13(9):663–671, 1984.
Tsuda et al., "The Effect of Pressure on the Dissociation of Weak Acids in Aqueous Buffers," Bulletin Chem. Soc., Japan, 49(11):2952–2955, 1976.
Whalley, "Some Comments on Electrostatic Volumes and Entropies of Solvation," J. Chem. Phys., 38(6):1400–1405, 1963.
Asano and le Noble, "Activation and Reaction Volumes in Solution," Chem. Reviews, 78(4):407–489, 1978.
Read, "Ionization Constants of Benzoic Acid from 25 to 250°C and 2000 Bar," J. Solution Chem., 10(7):437–450, 1981.

*Primary Examiner*—Jon P. Weber
*Attorney, Agent, or Firm*—Fish & Richardson, PC.

[57] ABSTRACT

The invention is based on the discovery that pressure-induced changes in the free ion activity of a solution can be used to reversibly modulate the rate or the equilibrium position of chemical reactions, including catalytic reactions and associating/dissociating reactions. Pressure-induced changes in free-ion activity can also be used to improve separation processes.

19 Claims, 2 Drawing Sheets

PRESSURE-MODULATED ION ACTIVITY

CROSS REFERENCE TO RELATED APPLICATION

This application is a continuation-in-part of U.S. Ser. No. 08/903,156, filed on Jul. 30, 1997, which is hereby incorporated by reference.

BACKGROUND OF THE INVENTION

This invention is in the general field of methods for modulating the rates of chemical reactions, enzymatic reactions, biomolecular separations, and purification processes conducted in buffers.

Buffers are compounds that reduce the sensitivity of free ion activity to perturbations caused by added or in situ generated ionic compounds. Reactions can be carried out in buffer solutions, especially if it is desired that the reaction rate or equilibrium position remain fairly constant.

One method for exerting control over free ion activity is to add ion-generating reagents (e.g., acids, bases, salts, or additional buffer compositions) to change the nature of the buffer solution at the elected time. This method is often effective for systems in which the free ion concentration is changed only a few times. Each addition of the reagents, however, increases contamination of the solution with salts and causes the reaction solution to become more dilute in reactants, which can slow the reactions over time. The effects of adding ionizing reagents are thus generally not strictly reversible, because additional reagents must be added if it is necessary to counteract the outcome of the addition of the first reagents. Addition and subsequent removal of salts require more labor, more complicated instruments, and, thus, more time and expense. Hence, it is generally desirable to avoid such additions.

SUMMARY OF THE INVENTION

The invention is based on the discovery that pressure-induced changes in the free ion activity of a solution can be used to reversibly modulate the rate or the equilibrium position of chemical and enzymatic reactions. Pressure-induced changes in free ion activity can also be used to improve separation processes. Changes in ion activity can be, for example, changes in the absolute concentration of an ion, or changes in the effective concentration of an ion as mediated by other processes (e.g., dielectric constants). The concept of ion activity is well known in the art of physical chemistry.

In general, the invention features a method for controlling the rate of a reaction in a solution by modulating the ionic activity of the solution. The method includes the steps of providing a solution that includes a buffer and reagents in a reaction vessel at an initial pressure and ionic activity; and changing the pressure within the vessel to a modified pressure to modulate the ionic activity of the solution. The change in the ionic activity is effective to change the reaction rate.

The buffer can be premixed with at least one of the reagents prior to mixing of all of the reagents. The buffer can have an absolute volume of ionization of at least 5, 15, or 25 milliliters per mole.

In some cases, changing the pressure to the modified pressure results in an increase or decrease in the pH (i.e., the negative logarithm of hydrogen ion concentration) or the pMg (i.e., the negative logarithm of the magnesium ion concentration) of the solution.

The buffer can include, for example, a lactone, a carbonate, carbon dioxide (in which case carbonic anhydrase can be added to the solution, e.g., to accelerate the reaction), a phosphate, a borate, an amine, a polyamine, a carboxylate, a salt, or other charged or easily ionizable compound, such as 1,4,6,12-tetraazacyclopentadecane or 1,1-cyclopropane dicarboxylic acid.

The chemical reactions that can be affected by the pressure-induced change in ionic activity include all chemical reactions. These include catalysis, whether by ions, inorganic materials, organic chemical materials, enzymes, or other catalytically effective entities; and association reactions, including solubility of a material in a solvent, binding of substrates to catalysts (including enzymes), association of substrates, cofactors or coreagents with a catalyst, or association between chemical entities, including association among any of ions, small molecules, macromolecules, and larger assemblies thereof.

Macromolecular associations can include associations of any macromolecules, including proteins, nucleic acids, carbohydrates, lipids, and synthetic macromolecules. In this context, macromolecules have a molecular weight in solution, by any system of measurement, of at least 1000 daltons, preferably 3000 daltons, more preferably 5000 daltons, and typically 10,000 daltons or more. Typical molecular weights of proteins and synthetic polymers include 30,000, 100,000, 500,000 and 1,000,000 daltons. There are no absolute upper molecular weight limits on entities whose association may be influenced by pressure-induced changes in ionic activity. Larger DNA molecules, for example, may have molecular weights ranging from 1000 base pairs (ca. 600,000 daltons) to 100,000,000 base pairs (chromosomes), and yet have their degree of base-pairing controllably regulated by pressure-induced ionic activity changes. Even large molecular assemblies, such as ribosomes, polymeric latexes and living or dead cells, can be induced to association or dissociate by such effects.

At least one of the reagents can be a catalyst (e.g., an enzyme) or a member of a binding pair. The activity of the enzyme can, for example, depend on the ionic activity in the solution. The enzyme can be an exonuclease or an exopeptidase, for example.

At least one of the reagents can be an antibody. The method can be used to increase the sensitivity or selectivity of antibody testing. The reagent can be a pH- or other ion-sensitive gel, the pore size of which can thus be modulated by pressure's effects on ion activity. Alternatively, the reagent can be a gel containing ionic moieties (e.g., amines or carboxylates) that can have their activities and/or conformation altered by pressure.

The pressure can be cycled repetitively between the modified pressure and a third pressure. The pressure cycling can additionally be coordinated with the cycling of a second parameter (e.g., temperature cycling, pressure cycling, etc.) between at least two (i.e., two, three, or more) values. The second parameter can also be pressure-dependent. The pressure cycling can, for example, control enzyme activity and the second cyclical process can control dissociation of the products of the enzymatic activity.

In another embodiment, the invention includes a method for controlling the equilibrium position of a reaction between at least two reagents. The method includes the steps of providing a solution comprising a buffer and the reagents in a reaction vessel at an initial pressure and ionic activity; and changing the pressure within the vessel to a modified pressure to modulate the ionic activity of the solution. The change in ionic activity is effective to change the equilibrium position of the reaction. In general, the interaction between any molecules forming a "binding pair" can be affected in a controllable manner by alteration of the ion activity by a change in pressure. The concept of a "binding pair" is known in the art.

The reaction can be, for example, a binding interaction (e.g., hybridization of two nucleic acid molecules to each other, such as DNA/DNA hybridization on a biochip), an immunoassay reaction, or protein denaturation. A binding interaction can also be used to purify a compound present in a sample containing both the compound and at least one impurity, if one of the reagents is the compound, another of the reagents is a solid support, and the method also includes washing the solid support to separate at least some of the impurity from the compound.

Another embodiment of the invention features a method for purification of a compound present in a sample containing both the compound and at least one impurity. The method includes the steps of introducing the sample onto a solid support at an initial pressure; establishing a pressure that enhances binding of either the compound or the impurity to the solid support; and washing the solid support to separate at least some of the impurity from the compound.

In some cases, the method can also include the steps of altering the pressure to dissociate the sample or impurity from the solid support, forming an eluate; and washing the contents of the vessel to separate the eluate from the solid support. These steps can be carried out, for example, to allow the compound to be isolated (e.g., if the binding of the compound to the solid support was enhanced by pressure) or to facilitate regeneration and/or reuse of the solid support.

It will be recognized that these processes, unlike classical ion exchange processes, do not require changes in the ionic content (mass concentration) of the elution medium, and thus minimize consumption of reagents, particularly in "washing" of the solid support with a new buffer to achieve an altered binding state of such solid support with respect to the materials being separated.

The solid support can be charged, or can be a neutral solid support capable of carried a charge. In either case, altering the pressure can, for example, alter the charge of the solid support. The solid support can be, for example, a resin (e.g., an anion-exchange resin), a liquid, a glass, a metal, a polymer (e.g., synthetic or natural, a biopolymer), silica gel, mineral, or other solid. In some cases, the solid support can simply be the walls of a reaction vessel. The solid support can be enmeshed or otherwise immobilized in a membrane, so as not to be affected by solvent or buffer flow.

The compound can be, for example, a single or double stranded nucleic acid polymer. For example, the compound can be DNA and the impurity RNA, or the compound can be RNA and the impurity DNA.

The sample can include free ions, and the compound can be fractionated by pressure modulation of the activity of the free ions. In this case, the compound can be a nucleic acid molecule such as DNA or RNA.

Yet another aspect of the invention is a method for controlling the rate of a chemical process in a solution (e.g., catalysis, association, or dissociation reactions, or protein denaturation), including selecting a buffer whose activity is effective in altering the rate in response to a defined change in the pressure at which the reaction is conducted; providing a solution that includes the buffer and reagents in a reaction vessel at an initial pressure; and altering the pressure to obtain the desired rate. The change in pressure can be so small as to not be sufficient to produce a significant change in rate in the absence of a selected buffer.

Free ions are charged atoms or molecules in solution. Free ions can be solvated but do not form aggregates in solution. More generally, the activity of the free ions of the solvent can be altered by controlled changes in pressure. The activity of an ion is a known concept. Alterations in activity can occur directly, by change in the absolute concentration of an ion, or indirectly, for example by a change in the properties of a solvent (such as a buffer) which alter the effective or apparent concentration of an ion with respect to a molecular interaction, such as a binding association or a catalytic reaction.

The concentration of a free ion is generally reported as the negative base ten logarithm. For example, pH is defined as the negative of the logarithm of the hydrogen atom concentration in a solution ($-\log[H^+]$). Similarly, pMg is the negative of the logarithm of the magnesium ion concentration ($-\log[Mg^+]$), and pOH is the negative logarithm of the hydroxide ion concentration ($-\log[OH^-]$). The activity of an ion or other material can be expressed as $pH_{app}$ or $pK_{app}$, where (for example) $pK_{app} = a \cdot pK$, and $a$ is the activity coefficient. The coefficient is generally less than one for isobaric (constant pressure) comparisons, but may be greater than one when solutions under differing pressures are being compared.

As used herein, the term "reaction" is used generically to describe chemical reactions, as well as specific and non-specific interactions. The methods disclose herein are applicable to both covalent and non-covalent binding interactions, and can affect both rate (kinetics) and equilibrium (thermodynamic quantities, such as $K_{eq}$ and its components, including $\Delta F$, $\Delta G$, and $\Delta S$) Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, technical manuals, and other references mentioned herein are incorporated by reference in their entirety. In case of conflict, the present application, including definitions, will control. In addition, the materials, methods, and examples are illustrative only and not intended to be limiting.

Advantages of pressure control of free ion activity include the use of pressure to alter ionization equilibrium constants (or activities) in a rapid and reversible manner; avoidance of the need to add fluids to the sample, thus eliminating dilution and contamination of samples with salts; use of pressure and pressure sensitive buffers without incurring the need to exchange fluids under high pressure, enabling the use of less costly and more durable pressure apparatuses.

Other features and advantages of the invention will be apparent from the following detailed description, and from the claims.

DETAILED DESCRIPTION OF THE INVENTION

Pressure-induced changes in pH and the activity of other ions can be used to reversibly modulate the rate and/or equilibrium position of chemical and enzymatic reactions. The extent of these changes depend on the absolute value of the ionization volume of the buffer compounds. Pressure-induced changes in free ion activity can also be used to improve separation processes involving ion-exchange resins. The ionization volumes can be estimated, based on fluorescence measurements of pH and other ion activities.

Buffers

Any buffer can be suitable for use in the invention, if its ionization volume allows the attainment of the desired change in ion activity at a practically achievable change in pressure. Preferred buffers have a large absolute value of ionization volume. The "absolute value" of an ionization volume is the magnitude of an ionization volume without regard to its sign.

Examples of buffers having large absolute values of ionization volumes include 1,4,8,12-tetraazacyclopentadecane and 1,1-cyclopropanedicarboxylic acid. Lactone and carbon dioxide-based systems are also suitable for use with the new methods, especially in organic solvents and at low pH in aqueous solvent systems.

The structural features that characterize a buffer having high absolute ionization volume include multiple charges, internal hydrogen bonding, and a change in conformation to exclude water upon ionization.

Pyrophosphate ion, 1,1-cyclopropanedicarboxylic acid, and tetraaza compounds have multiple charges. It is likely that multiply charged compounds have increased change in electrostriction (i.e., change in the dimension of the dielectric) upon ionization, resulting in a large absolute ionization volume.

Maleate and 3',3'-dimethylglutarate form internal hydrogen bond networks.

Compounds having cavities, such as derivatives of cyclodextrins or calixaranes, can be deformed by ion repulsion in the charged form to exclude water from the cavity. A tethered host-guest complex that is stabilized or disrupted by ionization can also exclude water. Proteins can also act as large ionization volume buffers by changing conformation to either a smaller or larger volume form upon ionization.

Figure 1:
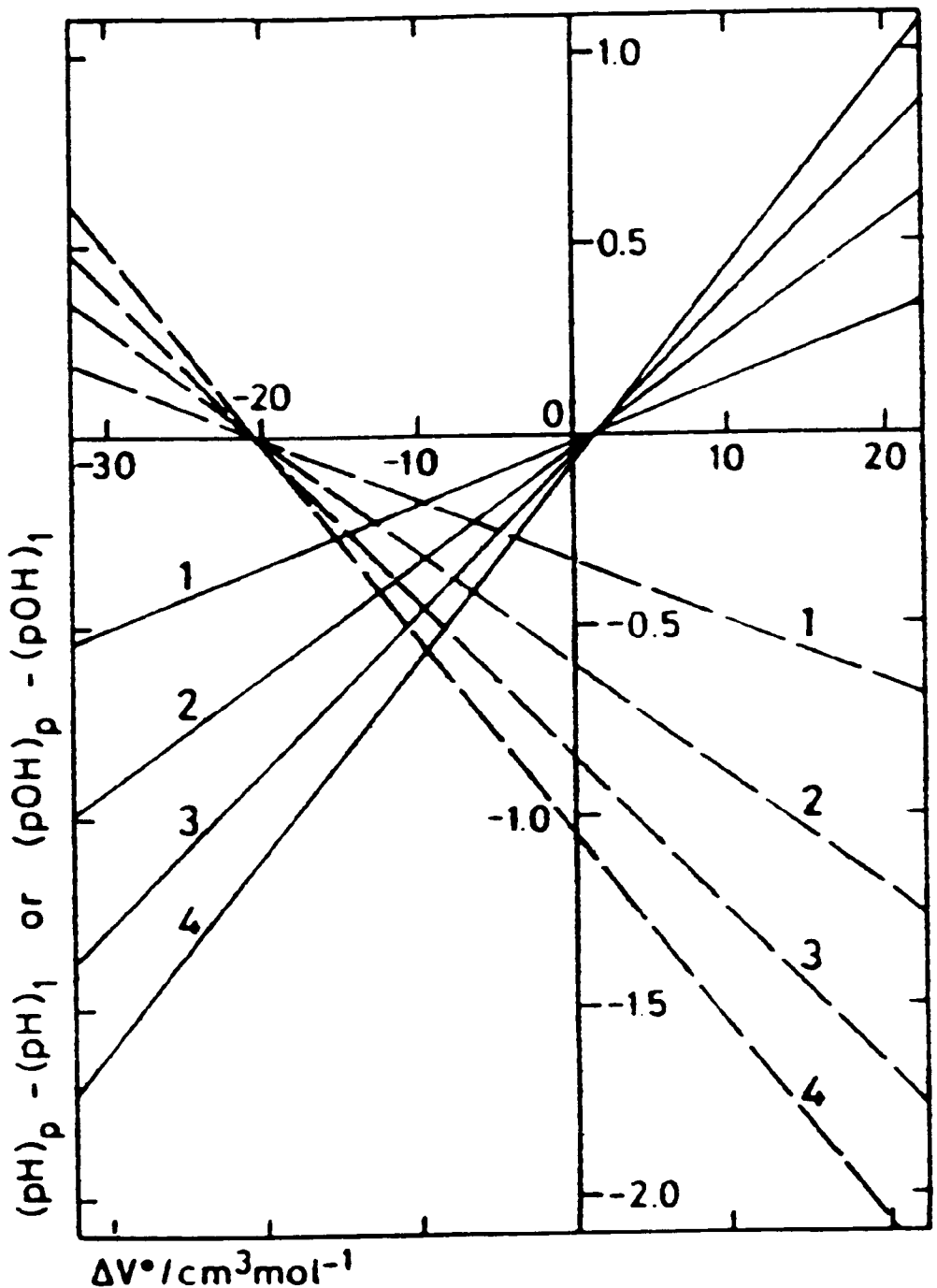
FIG. 1 is a plot of the dependence of pH and pOH on ionization volume at pressures from 1 to 4 kbar.

FIG. 1 shows the pH and pOH changes that can be achieved for buffers of varying ionization volumes at pressures of 1 through 4 kbar. The lines are generated from the following equations (Kitamura et al., *J. Solution Chem.*, 16:715–725, 1987; Hamman, *J. Solution Chem.*, 11:63, 1982):

$$(pH)_p - (pH)_i = (1.75 \times 10^{-5}) \Delta V^o P/(1+9.2 \times 10^{-5} P) + 354.3[(p/e^3)_p^{1/2} - (p/e^3)_i^{1/2}] \quad (1)$$

$$(pOH)_p - (pOH)_i = (1.75 \times 10^{-5})(-22.1 - \Delta V^o) P/(1+9.2 \times 10^{-5} P) + 354.3(T_p - T_i) \quad (2)$$

where e is the dielectric constant of water, p is density of water, $T_p - T_i = (p/e^3)_p^{1/2} - (p/e^3)_i^{1/2}$ and p and i represent conditions of high and low pressure, respectively. These equations are pertain to an ionized buffer with one unit of charge; the curves for more highly charged compounds have equal slope but are shifted vertically.

It is observed from FIG. 1 that pOH changes may be of larger magnitude than pH changes. Moreover, pH and pOH can be modulated simultaneously. Large changes (e.g., 100-fold) in [OH$^-$] can be achieved under moderate laboratory conditions of pressure.

Reaction Rates and Specificity

The rates of chemical and enzymatic reactions can be modulated by pressure-induced changes in the free ion activity of a solution. Ionization volumes and the magnitude of pressure-induced changes in pH can be detected by any convenient method of measurement, for example, by measurement of fluorescence excitation ratio.

Buffer systems producing large pressure-induced pH fluctuations have been discovered. High hydrostatic pressures alter equilibrium constants for ionization reactions of many buffers. In accord with Le Chatelier's principle, increased pressure causes the equilibrium of a reaction to shift toward a compound or mixture having the lowest volume among a set a alternatives. For most buffer systems, the lowest volume species or combination is generally the form having the most free ions, due to the fact that solvent volume is reduced by the influence of ionic charges (i.e., electrostriction). A plot of the natural logarithm of the molar dissociation constant against pressure yields a slope equal to the negative ionization volume divided by the product of the universal gas constant and the absolute temperature, or $\Delta K_d/\Delta P = -\Delta V^o/RT$.

A negative ionization volume indicates that the dissociated form of the buffer is lower in volume and favored by pressure whereas a positive ionization volume indicates that the form of the buffer in which the ion is bound has a lower volume and is favored by pressure.

To study pressure effects on chemical or biochemical equilibrium and kinetics, it is generally desirable to minimize changes in pH and pOH by selecting a buffer with a small absolute ionization volume (e.g., tris(hydroxymethyl)-aminomethane). However, for many applications it is desirable to find buffers that have large positive or negative ionization volumes. Pressure-induced pH/pOH changes can contribute greatly to pressure-induced enzyme inhibition or stimulation. Rapid, cyclic pressure-induced pH/pOH changes can also be used to disrupt protein aggregates and thereby promote refolding of partially or fully denatured proteins.

One determinant of the ionization volume of a reaction mixture is the decrease in volume of the ionized buffer due to electrostriction of the solvent (*Z. Physik Chem.*, 15:77, 1894). For example, the electrostriction change and absolute ionization associated with the fourth pK of pyrophosphate has an ionization volume of −28.9±0.2 whereas the third pK has an ionization volume of −20.7±0.4 and the second pKa has an ionization volume of −16.0±0.7 (*J. of Solution Chem.*, 16:715–725, 1987). Large negative ionization volumes can also result from intramolecular hydrogen bonding (Delben and Crescenzi, 1978) or from steric hindrance (le Noble and Asano, 1975). Electronic delocalization of a charged species (e.g., in resonance-stabilized ions) leads to smaller absolute ionization volumes.

The activity of a magnesium-dependent exonuclease can be regulated by pressure-induced changes. For example, a one unit, pressure-induced change in pMg around the pK for magnesium binding by the enzyme has the effect of changing the rate by about 10-fold if the enzyme requires only one magnesium ion, or 100-fold if the enzyme requires two magnesium ions. Similarly, a two unit change in pMg can have a 100- to 10,000-fold effect on rate. The magnesium effects can be combined with pressure-induced pH changes to give still larger effects on rate.

DNA Sample Preparation

DNA purification is an example of a separation that can be accomplished via the new methods. Contaminants in DNA samples can inhibit enzyme activity. For example, contaminants can cause template preparation procedures to fail to initiate or to terminate prematurely.

Anion-exchange resins can be used for DNA sample purification. For example, QIAGEN® resin includes a high density of positively charged DEAE moieties that tightly bind the negatively charged phosphates of the DNA backbone. The DNA remains tightly bound to the resin at medium salt concentration (e.g., 0.2 M NaCl) whereas impurities (e.g., RNA, chromosomal DNA, proteins, lipids, carbohydrates, or small metabolites) can be efficiently washed away.

Anion-exchange resins can be enmeshed in an inert matrix (e.g., a membrane), thereby facilitating sample handling.

The bound DNA molecules can be eluted by increasing the salt concentration (e.g., to 1.6 M NaCl). However, the eluted DNA ends up in a high salt solution, which can be incompatible with many molecular biological techniques (e.g., Sanger, fluorescent, and radioactive DNA sequencing systems, enzymatic reactions, in vitro packaging, restriction digestion, RFLP, transfection, microinjection, and in vitro transcription). The DNA is generally desalted in additional steps, such as precipitation with isopropanol. Removal of the isopropanol requires yet another step.

Extraction of RNA samples from tissues and cells requires stringent lysis conditions and the use of reagents (e.g., guanidinium isothiocyanate) to inactivate RNases. Hyperbaric conditions have been previously described in PCT Application WO 96/27432.

The new methods can also be used to improve existing protocols. For example, magnesium chloride concentration is an important variable in the effectiveness of metalloenzyme-mediated processes, such as DNA polymerase amplification of DNA by the polymerase chain reaction (PCR). The reduction of nonspecific primer-template interactions in the first cycle of the PCR reaction is critically important for high sensitivity, specificity, and yield. Magnesium concentration can be modulated by pressure using the new methods to determine the optimal concentration for the initial oligonucleotide primer hybridization before routine protocols are developed.

DNA Sequencing

The new methods enable cyclic modulation of free ion activity. For example, the activity of enzymes and antibodies can be controlled and synchronized by cycling the pressure. For example, pressure-induced pH and pMg changes can be used to activate exonuclease I of $E.$ $coli$. The new methods can also be combined with a cyclic process acting by a different mechanism (e.g., pressure/pH,pOH/temperature cycling for synchronized enzyme digestion or synthesis).

A discrete chemical step such as phosphate backbone hydrolysis can be controlled with a pressure-induced pH/pOH cycle; high activation volume steps (e.g., translocation of the enzyme along the DNA; structural change can be rate-limiting) can be controlled directly by pressure. For example, the hydrolysis step can be carried out at high pressure; the translocation can be carried out at low pressure at an inhibitory pH, and possibly high temperature.

Immunoassay

Acid dissociation followed by heating can be used to reduce false negatives in antibody testing. However, the heat can destroy some of the antigen and denature the antibody, thereby diminishing the accuracy of the tests. The combination of a pressure induced pH change (or other free ion change) with other pressure-induced changes can provide milder and thus more quantitative assays for this and other such assays. This method also complements the use of lactones, which tend to be useful at acid pH.

Higher temperatures can increase the absolute values of the ionization volumes; this phenomenon can be used to effect wider pH/pOH changes and can be combined with pressure mediated temperature stabilization of proteins to more rapidly get to equilibrium situations. In some cases, pressure-induced pH changes can enhance the effects of pressure changes. For example, prostate specific antigen (PSA) protein complexes can be disrupted through treatment with high pressure alone, although disruption or association can occur at a relatively lower pressure if a pressure-sensitive buffer is added to the reaction mixture. Following dissociation of endogenous complexes, for example, dissociated antigens can be detected with an antibody.

Binding and Chromatographic Separation

The new methods have many applications in binding and separation. For example, pressure-induced changes in ion exchange resins can be used in separations of DNA; pressure-induced changes in analyte charge by intrinsic or buffer-mediated mechanisms can be useful in hydrophobic chromatography; pressure-induced pH changes can modulate denaturation volume for stationary phase biomolecules, allowing chiral compounds to be purified by immobilized enzymes; and pressure-induced pH changes can be used to decrease the pressure required for disruption of antibody complexes.

Without further elaboration, it is believed that one skilled in the art can, based on the above description, utilize the present invention to its fullest extent. The materials, methods, examples, and the specific embodiments are, therefore, to be construed as merely illustrative, and not limiting of the remainder of the disclosure in any way whatsoever.

EXAMPLES

Example 1

The experiment described below was carried out to demonstrate the use of fluorescence excitation ratio pH measurements to estimate ionization volumes and measure pressure-induced pH changes.

Procedure

Buffer standards, including imidazole, 1,3-bis[tris-(hydroxymethyl)-methylamino]propane ("bis-tris" propane), potassium bicarbonate, cacodylic acid, 3',3'-dimethylglutarate, and potassium pyrophosphate (all from Aldrich, Milwaukee, Wis.) were made to activities of 20 to 75 mM with the pH in each instance being no more than 0.5 units from the pK of the buffer (i.e., pH 5–7). Fluorescein (Aldrich) was added to a concentration of 45 nM by addition of 75 $\mu$l of 900 nM stock solution to 1425 $\mu$l of each buffer.

The samples were mixed well by syringe and loaded into a quartz bottle (ISS, Champaign, Ill.) having a polyethylene cap. The cap was firmly placed on the bottle so that it overlapped the bottle's neck by several millimeters and placed in an ethanol-filled, high-pressure spectroscopic cell with sapphire optical windows (ISS, Champaign, Ill.). The cap of the pressure cell was secured with a 50 ft-lb torque wrench, placed into an ISS PC1 fluorometer and attached by a flexible metal hose to a hand-cranked pressure generator (High Pressure Equipment, Erie, Pa.) with a digital pressure sensor (Sensotec). Ethanol was employed as a pressurizing medium.

The ratio of excitation at 490 nm to 450 nm was measured on an excitation monochrometer and observed by monitoring emission at 520 nm. Measurements were made every 5000 psi to at least 20000 psi. The fluorescence excitation ratio was plotted against pressure and the slope in the linear range (1.7 to 3.8) was estimated by regression. The pressure sensitivities (i.e., absolute ionization volumes) were used to make a standard curve by plotting the sensitivities against the ionization volumes of the test buffers. The x-intercept was taken to be the ionization volume for fluorescein.

TABLE 1

| Compound | Ionization Volume (ref) |
|---|---|
| "bis-tris" propane | 10.5 |
| imidazole | 1.8 |
| cacodylic Acid | −13.2 |
| pyrophosphate | −20.7 |
| 3',3'-dimethylglutarate | −25.0 |
| potassium bicarbonate | −27.6 |

A linear fit of the plot of the pressure sensitivity in the fluorescein excitation ratio against the ionization volumes of the standards (FIG. 2) gave a slope of $1.606 \times 10^{-6}$ (ratio units)·$psi^{-1}$·($ml \cdot mol^{-1}$) and a y-intercept of $1.35 \times 10^{-5}$ (ratio units)·$psi^{-1}$. The x-intercept was −8.4, which represents the ionization volume for fluorescein.

Ionization volumes for various buffers were measured using the equation of the standard curve (Table 2).

TABLE 2

| Buffer | pK | pH | $\Delta V_{ion}$ (ml/mol) |
|---|---|---|---|
| 1,1 cyclopropanedicarboxylic acid | 7.5 | 6.5 | −28.9 |
| 1,4,8,12 tetraaza-cyclopentadecane | multiple | 5.1 | +29.9 |

Results

The negative ionization volume for 1,1-cyclopropanedicarboxylic acid (Aldrich) is the largest pressure effect reported for an ionization with a pK of less than 9. The ionization volume of 1,1-cyclopropanedicarboxylic acid is equal to the $\Delta V_{ion}$ for the fourth ionization of phosphate while having only half the charge in the ionized form. Additionally, the large positive ionization volume observed for 1,4,8,12-tetraazacyclopentadecane (Aldrich) appears to be the largest known positive ionization volume.

The fluorescein excitation ratio can be used as a model for an enzymatic reaction that requires the ionization of an acidic group. In the case of 1,4,8,12-tetraazacyclopentadecane, the ionization of fluorescein exhibited the equivalent of about three pH units change with the application of 55,000 psi pressure; the excitation ratio at the highest pressure was 4.6.

Figure 2:
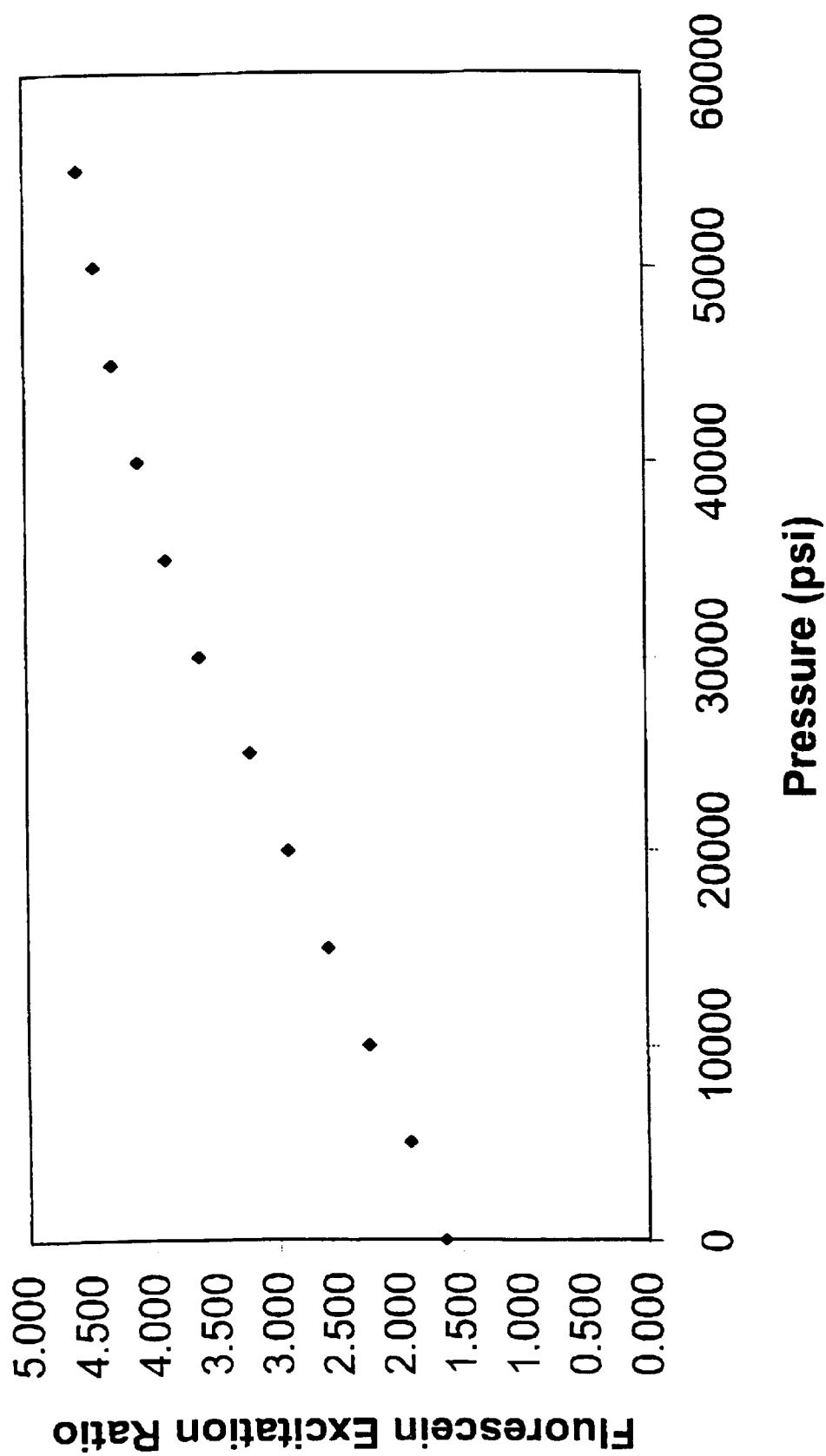
FIG. 2 is a plot of the fluorescence excitation ratio of a 1,4,8,12-tetraazacyclopentadecane solution as a function of pressure

FIG. 2 shows the fluorescence excitation ratio of 20 mM 1,4,8,12-tetraazacyclopentadecane (initial pH of 5.1) at various pressures. The fluorescence was measured at 490 and 450 nm, and emission was monitored at 520 nm. The excitation ratio decreased to the initial value upon depressurization, demonstrating that the changes are reversible. The excitation ratio at 55,000 psi is consistent with a pH of about 8. Thus, a pH change of approximately 3 units was observed.

Example 2

A solution containing magnesium salts is obtained. A negatively charged magnesium chelating compound having a pK for magnesium dissociation that is less than one unit from the solution's pMg is added to the solution, creating a magnesium buffering system.

Because the dissociated magnesium ions and chelating compound are more charged than the bound complex, solvent electrostriction decreases the volume of the dissociated complexes, making the free ions favorable under hyperbaric conditions. Pressure can thus be used to reversibly alter the free magnesium ion concentration.

Examples of suitable magnesium-buffering chelating compounds include sulfate, oxalate, and aspartate. These compounds are useful in the mM concentration range needed for the activation of exonucleases, for example.

Example 3

The rate of reaction of a magnesium-dependent exonuclease is measured by observing the change in absorbance of 260 nm light in a high pressure spectroscopic cell upon release of nucleoside monophosphate products. A reaction mixture is made containing 45 μl of λ-phage DNA, 150 μl of 10X buffer (containing 100 mM Tris-HCl at pH 8, 100 mM β-mercaptoethanol, 10 mM magnesium oxalate, and 10 mM potassium oxalate), and 50 units of exonuclease III from E. coli (USB, Cleveland, Ohio). The slope of the reaction is measured at atmospheric pressure, 10,000 psi, 20,000 psi, 30,000 psi, 40,000 psi, and 55,000 psi. The reaction rate increases at moderate pressures, at which magnesium is released.

Other Embodiments

It is to be understood that while the invention has been described in conjunction with the detailed description thereof, that the foregoing description is intended to illustrate and not to limit the scope of the appended claims. Other aspects, advantages, and modifications are within the scope of the following claims.

What is claimed is:

1. A method for purification of a compound present in a sample containing both the compound and at least one impurity, the method comprising:

introducing the sample onto a solid support in the presence of a buffer having an absolute volume of ionization of at least fifteen milliliters per mole;

establishing a pressure that enhances binding of either the compound or the impurity to the solid support in the presence of the buffer; and washing the solid support at the established pressure to separate at least some of the impurity from the compound.

2. A method of claim 1, further comprising:

altering the pressure to a second pressure to dissociate whichever of the compound or impurity was enhancedly bound from the solid support to form an eluate; and washing the solid support to separate the eluate from the solid support.

3. A method of claim 2, wherein the established pressure enhances the binding of the compound to the solid support.

4. A method of claim 2, wherein the second pressure is greater than ambient pressure.

5. A method of claim 1, wherein the solid support is charged.

6. A method of claim 5, wherein the charge of the solid support is pressure-dependent.

7. A method of claim 5, wherein the solid support is an anion-exchange resin.

8. A method of claim 1, wherein the compound is a single or double stranded nucleic acid polymer.

9. A method of claim 1, wherein the solid support is enmeshed in a membrane.

10. A method of claim 1, wherein the solid support is silica gel.

11. A method of claim 1, wherein the compound is DNA and the impurity is RNA.

12. A method of claim 1, wherein the compound is RNA and the impurity is DNA.

13. A method of claim 1, wherein the sample includes free ions, and the method further comprises using pressure to modulate the activity of the free ions.

14. A method of claim 13, wherein the compound is nucleic acid.

15. A method of claim 14, wherein the nucleic acid is DNA.

16. A method of claim 14, wherein the nucleic acid is RNA.

17. A method of claim 1, wherein the pK of the solid support is pressure dependent.

18. A method of claim 1, wherein the established pressure is greater than ambient pressure.

19. A method of claim 1, wherein the pressure is established prior to introducing the sample onto the solid support.

* * * * *